(12) United States Patent
Demirci et al.

(10) Patent No.: US 12,036,000 B2
(45) Date of Patent: Jul. 16, 2024

(54) METHOD OF PHOTOACOUSTIC IMAGING INTRAOCULAR TUMORS INCLUDING BACK-PROJECTION RECONSTRUCTION TO MEASURE HETEROGENEITY

(71) Applicant: THE REGENTS OF THE UNIVERSITY OF MICHIGAN, Ann Arbor, MI (US)

(72) Inventors: Hakan Demirci, Pinckney, MI (US); Guan Xu, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 88 days.

(21) Appl. No.: 16/304,805

(22) PCT Filed: May 25, 2017

(86) PCT No.: PCT/US2017/034476
§ 371 (c)(1),
(2) Date: Nov. 27, 2018

(87) PCT Pub. No.: WO2017/205626
PCT Pub. Date: Nov. 30, 2017

(65) Prior Publication Data
US 2020/0315461 A1    Oct. 8, 2020

Related U.S. Application Data

(60) Provisional application No. 62/342,471, filed on May 27, 2016.

(51) Int. Cl.
*A61B 5/00*        (2006.01)
*A61B 8/10*        (2006.01)
(Continued)

(52) U.S. Cl.
CPC .............. *A61B 5/0095* (2013.01); *A61B 8/10* (2013.01); *G01N 29/2418* (2013.01); *G01N 29/348* (2013.01)

(58) Field of Classification Search
CPC ....... A61B 5/0095; A61B 8/10; A61B 8/4483; G01N 29/348; G01N 29/2418;
(Continued)

(56) References Cited

U.S. PATENT DOCUMENTS 5,840,023 A    11/1998  Oraevsky et al.
8,672,851 B1 *  3/2014  Quirk .................. A61B 8/4218
                                                     600/459

(Continued)

FOREIGN PATENT DOCUMENTS

WO    WO-2008062199 A2    5/2008

OTHER PUBLICATIONS

Huang, H., Bustamante, G., Peterson, R., & Ye, J. Y. (2015). An adaptive filtered back-projection for photoacoustic image reconstruction. Medical physics, 42(5), 2169-2178. https://doi.org/10.1118/1.4915532. (Year: 2015).*

(Continued)

*Primary Examiner* — Christopher Koharski
*Assistant Examiner* — Richmond J Van Winter
(74) *Attorney, Agent, or Firm* — Harness, Dickey & Pierce, P.L.C.

(57) ABSTRACT

A method of diagnosing intraocular tumors including illuminating a tissue sample using a pulsed light source resulting in output of heat and thermoelastic expansion of the tissue sample. The thermoelastic expansion of the tissue sample produces propagating waves in ultrasonic frequencies. The propagating waves are acquired using an ultrasound system and back-projection reconstruction, thereby (Continued)

mapping anatomies with optical contrast at ultrasonic resolution to image intraocular tumors.

4 Claims, 8 Drawing Sheets

(51) Int. Cl.
　　　*G01N 29/24*　　　(2006.01)
　　　*G01N 29/34*　　　(2006.01)
　　　*A61B 8/00*　　　(2006.01)
　　　*G01N 21/17*　　　(2006.01)
　　　*G01N 29/46*　　　(2006.01)
(58) Field of Classification Search
　　　CPC ............... G01N 21/1702; G01N 29/46; G01N 2291/015; G01N 2291/106; G01N 2291/02475
　　　See application file for complete search history.

(56) References Cited

U.S. PATENT DOCUMENTS

| | | | | |
|---|---|---|---|---|
| 9,740,662 | B2* | 8/2017 | Smigelski | G06F 17/141 |
| 2002/0193678 | A1 | 12/2002 | Kruger | |
| 2008/0123083 | A1* | 5/2008 | Wang | A61B 5/0091 356/73 |
| 2009/0318831 | A1* | 12/2009 | Aoki | A61B 1/05 600/106 |
| 2010/0049044 | A1* | 2/2010 | Burcher | A61B 5/0095 600/437 |
| 2010/0094134 | A1* | 4/2010 | Zhu | A61B 8/4416 600/473 |
| 2010/0245766 | A1* | 9/2010 | Zhang | A61B 8/10 73/649 |
| 2010/0285518 | A1 | 11/2010 | Viator et al. | |
| 2011/0306857 | A1* | 12/2011 | Razansky | A61B 5/0095 600/407 |
| 2011/0306865 | A1 | 12/2011 | Thornton et al. | |
| 2012/0271204 | A1* | 10/2012 | Peyman | A61B 5/1455 601/2 |
| 2015/0366458 | A1* | 12/2015 | Kellnberger | G01N 29/2418 600/407 |
| 2016/0022976 | A1* | 1/2016 | Peyman | A61K 47/6929 600/407 |
| 2016/0262628 | A1* | 9/2016 | Wang | A61B 8/4245 |

OTHER PUBLICATIONS

Alic L, Niessen WJ, Veenland JF. (2014). Quantification of heterogeneity as a biomarker in tumor imaging: a systematic review. PLoS One. Oct. 20, 2014;9(10): e110300. doi: 10.1371/journal.pone.0110300. PMID: 25330171; PMCID: PMC4203782. (Year: 2014).*

Huang, H., Bustamante, G., Peterson, R.,& Ye, J.Y. (2015). An adaptive filtered back-projection for photoacoustic image reconstruction. Medical physics, 42(5), 2169-2178. httos://doi.org/10.1118/1.4915532. (Year: 2015).*

Alic L, Niessen WJ, Veenland JF. (2014). Quantification of heterogeneity as a biomarker in tumor imaging: a systematic review. PLoS One. Oct. 20, 2014; 9(10): e110300. doi:10.1374/journal.pone.0110300.PMID:25330171;PMCID:PMC4203782. (Year: 2014).*

G. Paltauf, J. Viator, S. Prahl, S. Jacques. (2002). Iterative reconstruction algorithm for optoacoustic imaging. J. Acoust. Soc. Am., 112 (2002), pp. 1536-1544. doi: 10.1121/1.1501898. (Year: 2002).*

Kim, Chulhong et al. "In vivophotoacoustictomograph yofchemicals:high-resolutionfunctionalandmolecularopticalimaging atnewdepths." Chemicalreviews1105(2010):2756-82. (Year: 2010).*

Xu M, Wang LV. Universal back-projection algorithm for photoacoustic computed tomography. Phys Rev E Stat Nonlin Soft Matter Phys. Jan. 2005; 71(1 Pt 2):016706. (Year: 2005).*

Kumon RE, Deng CX, Wang X. Frequency-domain analysis of photoacoustic imaging data from prostate adenocarcinoma tumors in a murine model. Ultrasound Med Biol. 2011:37(5):834-839. doi: 10.10164.ultrasmedbio.2011.01.012 (Year: 2011).*

Natalie Baddour, "Theory and analysis of frequency-domain photoacoustic tomography", The Journal of the Acoustical Society of America123, 2577-2590 (2008) https://doi.org/10.1121/1.2897132 (Year: 2008).*

Silverman RH, Kong F, Chen YC, et al. High-resolution photoacoustic imaging of ocular tissues. Ultrasound Med Biol. 2010; 36(5):733-742. doi: 10.1016/.ultrasmedbio.2010.02.006 (Year: 2010).*

International Search Report and Written Opinion of the International Searching Authority issued in PCT/US2017/034476, dated Aug. 23, 2017; ISA/KR.

Zerda et al. "Photoacoustic Ocular Imaging." Opt. Lett. Feb. 1, 2010. 35(3): 270-272.

Hu et al. "Label-free photoacoustic ophthalmic angiography." Jan. 1, 2010. vol. 35, No. 1, Optics Letters.

Yang et al. "Noninvasive photoacoustic detecting intraocular foreign bodies with an annular transducer array." Opt Express. Jan. 14, 2013. 21(1): 984-91.

Zhang et al. Photoacoustic Ophthalmoscopy for In Vivo Retinal Imaging: Current Status and Prospects. Ophthalmic Surgery, Lasers & Imaging: The Official Journal of the International Society for Imaging in the Eye, 42(0), S106-S115.

Kumon et al. Frequency-Domain Analysis of Photoacoustic Imaging Data From Prostate Adenocarcinoma Tumors in a Murine Model. Ultrasound in Medicine & Biology. vol. 37, Issue 5. May 2011. 834-839.

Feleppa et al. "Diagnostic Spectrum Analysis in Ophthalmology: A Physical Perspective." Ultrasound in Med & Biol. vol. 12, No. 8. 623-631.

Silverman et al. "High-Resolution Photoacoustic Imaging of Ocular Tissues." Ulstrasound in Med. & biol. May 2010. 36(5): 733-742.

Lihong V. Wang et al. "Photoacoustic Tomography: In Vivo Imaging from Organelles to Organs" Source: Science, Mar. 23, 2012, New Series, vol. 355, No. 6075 (Mar. 23, 2012), pp. 1458-1462.

* cited by examiner

METHOD OF PHOTOACOUSTIC IMAGING INTRAOCULAR TUMORS INCLUDING BACK-PROJECTION RECONSTRUCTION TO MEASURE HETEROGENEITY

CROSS-REFERENCE TO RELATED APPLICATIONS

This application is the U.S. National Phase Application under 35 U.S.C. 371 of International Application No. PCT/US2017/034476, filed on May 25, 2017, which claims the benefit of U.S. Provisional Application No. 62/342,471, filed on May 27, 2016. The entire disclosures of the above applications are incorporated herein by reference.

FIELD

The present disclosure relates to the use of photoacoustics to image intraocular tumors.

BACKGROUND AND SUMMARY

This section provides background information related to the present disclosure which is not necessarily prior art. This section also provides a general summary of the disclosure, and is not a comprehensive disclosure of its full scope or all of its features.

Intraocular tumors are relatively rare, but life-threatening conditions. The accurate diagnosis of intraocular tumors is crucial in the management and follow-up of the patient. The diagnosis of intraocular tumors is usually based on clinical examination with imaging techniques. Current imaging techniques provide detailed structural, but limited functional and histochemical information. Additionally, the current imaging technologies have limitations of penetration. The technology of the present invention will provide functional and histochemical information of the tumor and improve the diagnosis.

Photoacoustic (PA) imaging is based on the photoacoustic effect where a light pulsed (such as from a pulsed laser) source is used to produce mechanical vibration inside of a medium and tissue in the ultrasound range due to transient thermal absorption. By using a laser, an image can be reconstructed by "listening to the light" using ultrasound equipment, each color of light makes a different ultrasound signal. Through spectral analysis of the PA signals, functional information (such as histopathology) from the tissue imaged can be obtained. The present invention applies PA spectral analysis to quantify microscopic structures of each individual histochemical component for different cancers in intraocular tumors, allowing for accurate diagnosis for various cancers of the eye.

More particularly, optically (photo-) induced ultrasound (-acoustic) imaging, namely photoacoustic imaging (PAI), is an emerging, non-ionizing, non-invasive, low cost, imaging technology, with the capability of providing both structural and functional information. In PAI, the tissue sample is illuminated by a pulsed light source. When absorbed by the target sample, the optical energy converts to heat and causes a tiny and quick thermoelastic expansion of the sample tissue. The thermoelastic expansion leads to propagating waves in ultrasonic frequencies, namely PA waves. By acquiring PA waves with instruments for US, the anatomic structures with different optical contrasts can be mapped at ultrasonic resolution. Following procedures similar to those in US, PA spectral analysis (PASA) can be performed by analyzing the frequency spectrum of the PA signal from the tissue. PASA demonstrated the capability of quantifying the microscopic architectures formed by each individual histochemical component in biological tissues.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Intraocular tumors can be a life-threatening condition that requires accurate diagnosis. Current technology can provide a detailed structural view of the eye, but is limited in providing functional information, such as what types of cells or chemicals are inside the eye. The disclosed technology is an imagining technique that not only offers detailed structural images of tumors in the eye, but also gives information about what type of cancer—differentiating healthy and cancerous tissue—in a safe, non-invasive approach. Since the disclosed technology uses ultrasound equipment, it has the potential to be drastically less expensive and more compact than current functional imaging approaches.

The disclosed technology offers several advantages over competing technologies for cancer detection within the eye, one of which is that it is non-invasive, compared to methods that involve a biopsy. Another is that the disclosed technology uses ultrasounds (by taking advantage of the photoacoustic effect), which offers the ability to image deep in the tissue with the potential to be drastically less expensive than imaging techniques that involve radiation (such as Computerized Tomography using X-rays) or super powerful magnets (Magnetic Resonance Imaging). Compared to traditional ultrasound imaging, the disclosed technology is able to provide histopathological information (which is crucial for cancer diagnosis) in addition to anatomical information. The disclosed technology also compares favorably with newer advanced imaging modes, such as Optical Coherence Tomography (OCT), which uses optical light for imaging and functional measurements, as OCT may be limited to smaller tissue depths compared to the disclosed technology and provides histopathological information about the tumor.

Imaging System

Figure 1A:
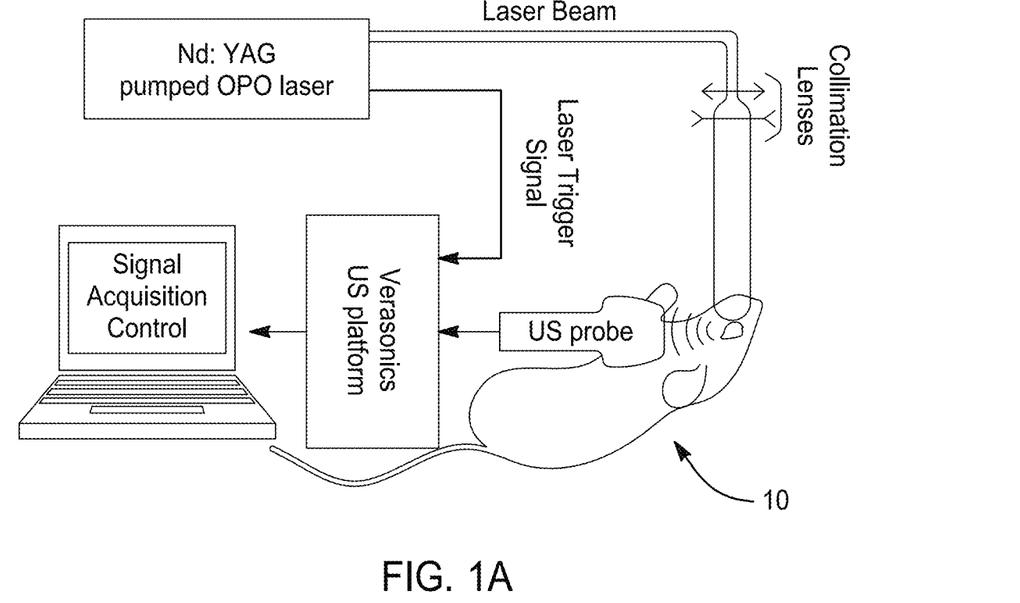
FIG. 1A is an experiment system schematic of a mouse experiment in vivo.
Figure 1B:
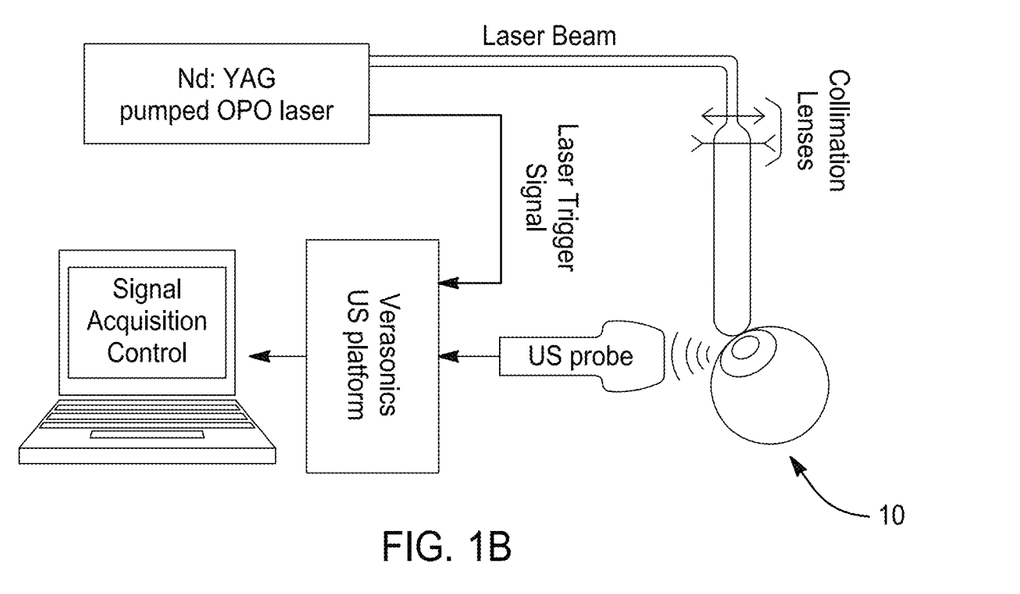
FIG. 1B is an experiment system schematic of human eye globe imaging ex vivo.
Figure 5A:
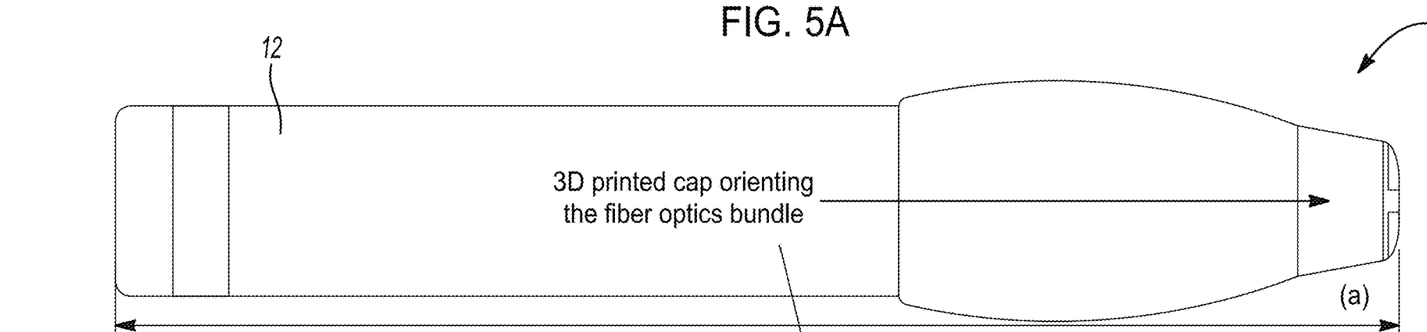
FIG. 5 illustrates a photoacoustic imaging system according to the principles of the present teachings.
Figure 5B:
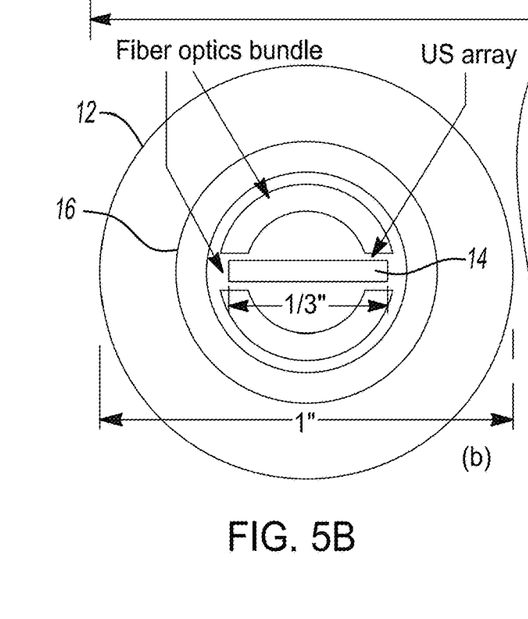
Figure 5C:
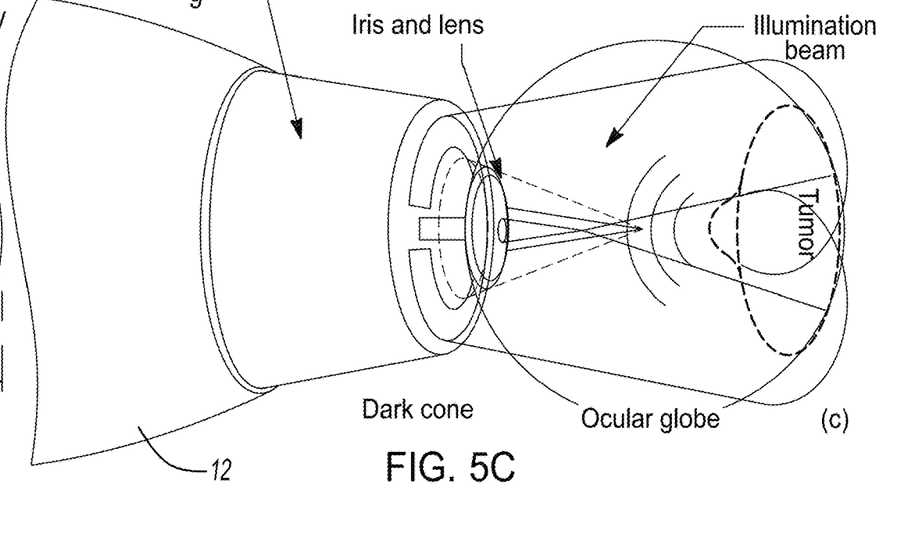

As illustrated in FIGS. 1 and 5, a photoacoustic imaging system 10 is provided according to the principles of the present teachings. In some embodiments, the photoacoustic imaging system 10 can comprise a probe 12 having external dimensions of a clinical US probe. The probe 12 can output photoacoustic-ultrasound signals, which are acquired by a convex US transducer array 14. The transducer array 14 can comprise an exemplary 128 elements with an exemplary broadband frequency range of 20 MHz with 80% bandwidth. The convex array 14 can cover 50 degree angle in front of the probe 12. Two fiber optics bundles 16, with arc-shaped emission ends, can be integrated to the front end of probe 12 to deliver illumination for PA measurement. The US array 14 can be positioned over the Iris. US mode alone can located the lesions. The illumination is afterwards turned on for PAI. The two beams will formulated a dark cone circumventing the Iris area, avoiding focused optical energy at the back of the eye.

Additional prototype testing was completed of photoacoustic imaging system 10 using an US platform. The system was successfully implemented in liver imaging in small animals and finger joint imaging in human subjects. A wavelength tunable Optical parametric oscillator (OPO) laser pumped by a second harmonic of a pulsed neodymium-doped aluminum garnet laser was used as the illumination source for PAI. The tunable wavelength range of the laser is 680-950 nm and 1200-2400 nm. The laser energy at the surface of the eye globes in all the experiments was maintain below 20 mJ/cm$^2$, which is the safety limit established by American National Standard Institute (ANSI). Considering the limited imaging depth for ocular imaging and the frequency range for clinical ocular US imaging, two high frequency linear array transducers were used. A CL15-7 (linear array with later dimension of 2 cm) working at a central frequency of 11.25 MHz was used for human eye imaging ex vivo. An L22-14v (linear array with later dimension of 1.5 cm) working at a central frequency of 18 MHz were used for mouse eye imaging in vivo. The temporal sampling rates are four times higher than the central frequency. With the temporal sampling rates the system can acquire 2D B-scan PAI and US images simultaneously and continuously, both in truly real-time fashion. Limited by the laser repetition rate, a frame rate of 10 Hz was used in the scanning procedures in this study.

Mouse Study

Figure 2:
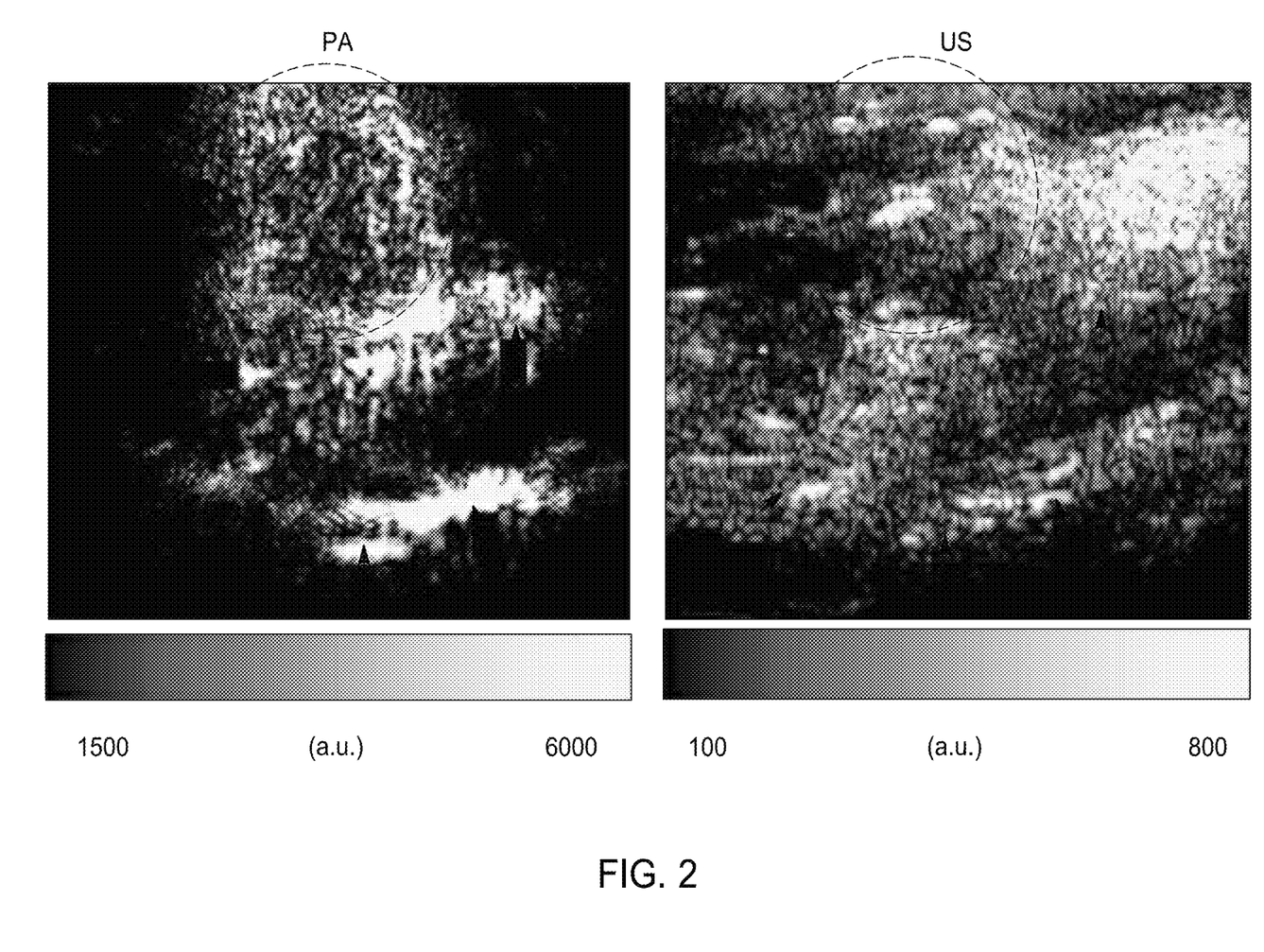
FIG. 2 is PA and US images of retinoblastoma tumors in mice. The PA image was acquired at 720 nm. The dashed circle marks the contour of the eye globe. The arrows mark the skull of the mouse.

A transgenic mouse model, BLH-SV40 Tag, was first used to examine the capability of the system in imaging eye tumors. The mice spontaneously develop reinoblastoma in the eye globe filling the eye globe. The eye globes were imaged using the system of the present teachings. During the experiment, the mice were anesthetized by inhaling 1-5% vaporized isoflurane. As illustrated in FIG. 2A, the imaging plane was first confirmed by US where the contours of the mouse eye globes were found. The laser beam was projected perpendicular to the US imaging plane. As illustrated in FIG. 2B, the PA images were acquired by averaging 10 times for improved signal-to-noise ratio (SNR). The laser power energy was recorded by an optical power meter for later image intensity calibration.

Human Eye Globe Imaging

De-identified, enucleated human ocular globes were acquired through standard procurement procedures. The CL15-7 with lateral dimension of 2 cm instead of the Lv22-14 was used due to the larger dimension of the human eye globe. The optical illumination was delivered through an 8 mm diameter fiber optics to the eye globe surface (illustrated in FIG. 1B) at the intensity of 20 mJ/cm$^2$. During the imaging experiment, the tumor inside the globe was first located in US imaging. The illumination direction was afterwards optimized for PA imaging.

Results

Representative Images of Retinoblastoma Tumors in Mice

FIGS. 2A and 2B shows a set of representative PA-US images of the eye globes. In addition to the eye globe, due to the diffusion of the photons and the strong optical absorption of the bone, the skull of the mouse was also illustrated in the PA images. The average pixel intensity as a representation of the total optical absorption of the eye globes were displayed and statistically study in FIG. 3A.

Representative Images of Human Retinoblastoma and Uveal Melanoma Tumors

Figure 3A:
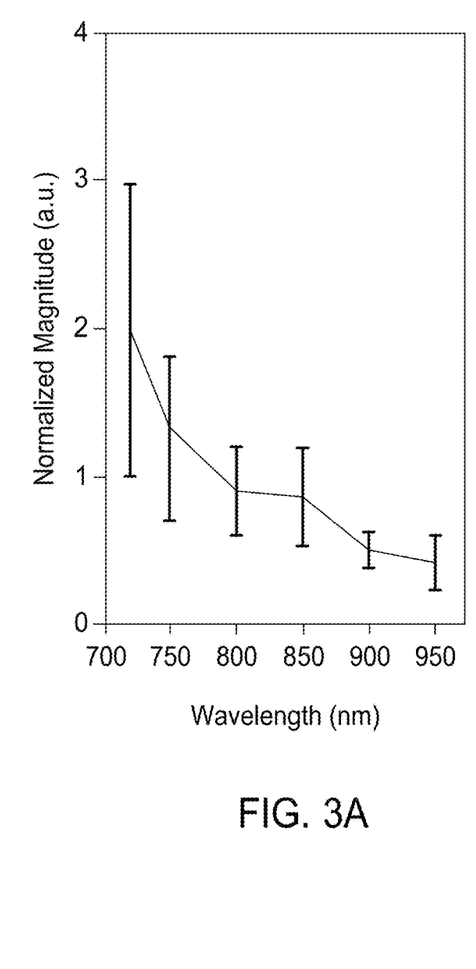
FIG. 3A shows relative optical absorption spectra of retinoblastoma in mice.
Figure 3B:
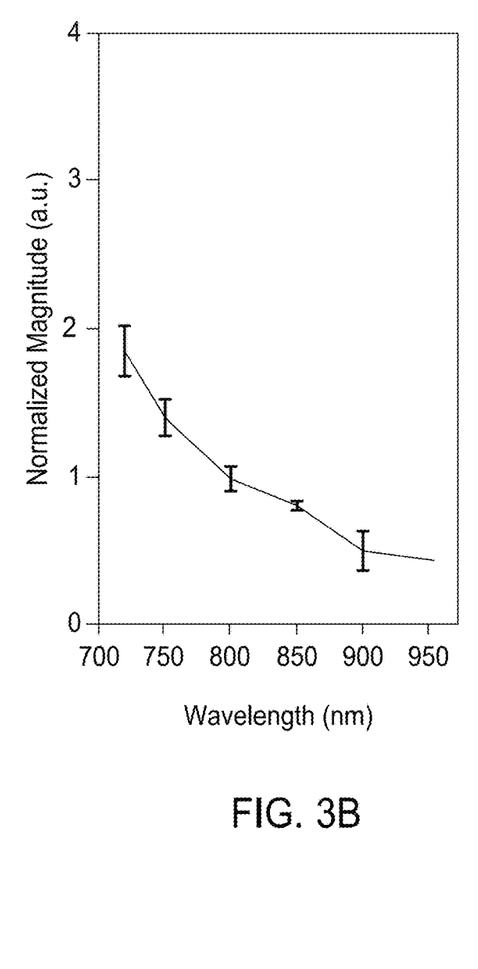
FIG. 3B shows relative optical absorption spectra of retinoblastoma in humans.
Figure 3C:
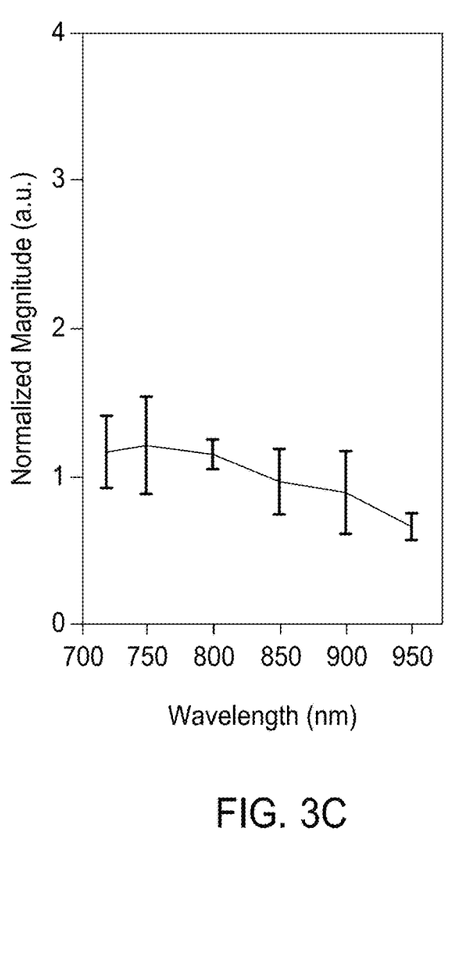
FIG. 3C shows relative optical absorption spectra of melanoma in humans.
Figure 4:
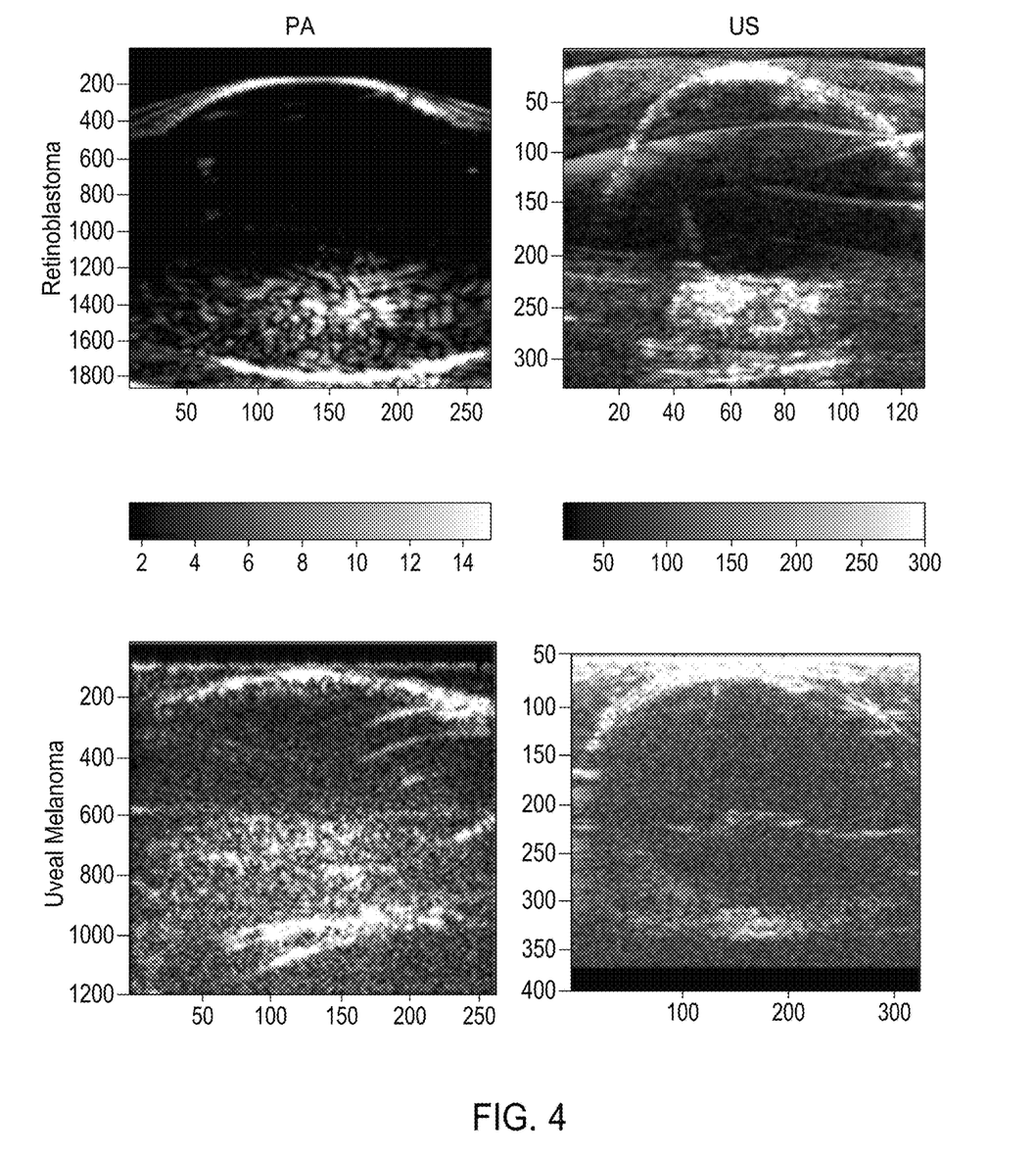
FIG. 4 shows PA and US images of ex vivo human ocular globes with retinoblastoma and uveal melanoma.

FIGS. 3A-3C illustrate the representative PA-US images of the ex vivo human eye globes containing retinoblastoma and uveal melanoma tumors. PA and US images show similar tumor contours. In US image, the melanoma tumor appear hypoechoic, whereas the retinoblastoma spear hyperechois. However such difference can hardly be quantified with respect to the molecular components of the tumors. In the PA images, both tumors appear bright. However, the total optical absorption spectra in FIGS. 3B and 3C generated by the multi-wavelength PA measurements provide quantitative differentiation between the two types of tumors.

Representative US and PA Images of Ex Vivo Human Ocular Globes with Tumors

Figure 6:
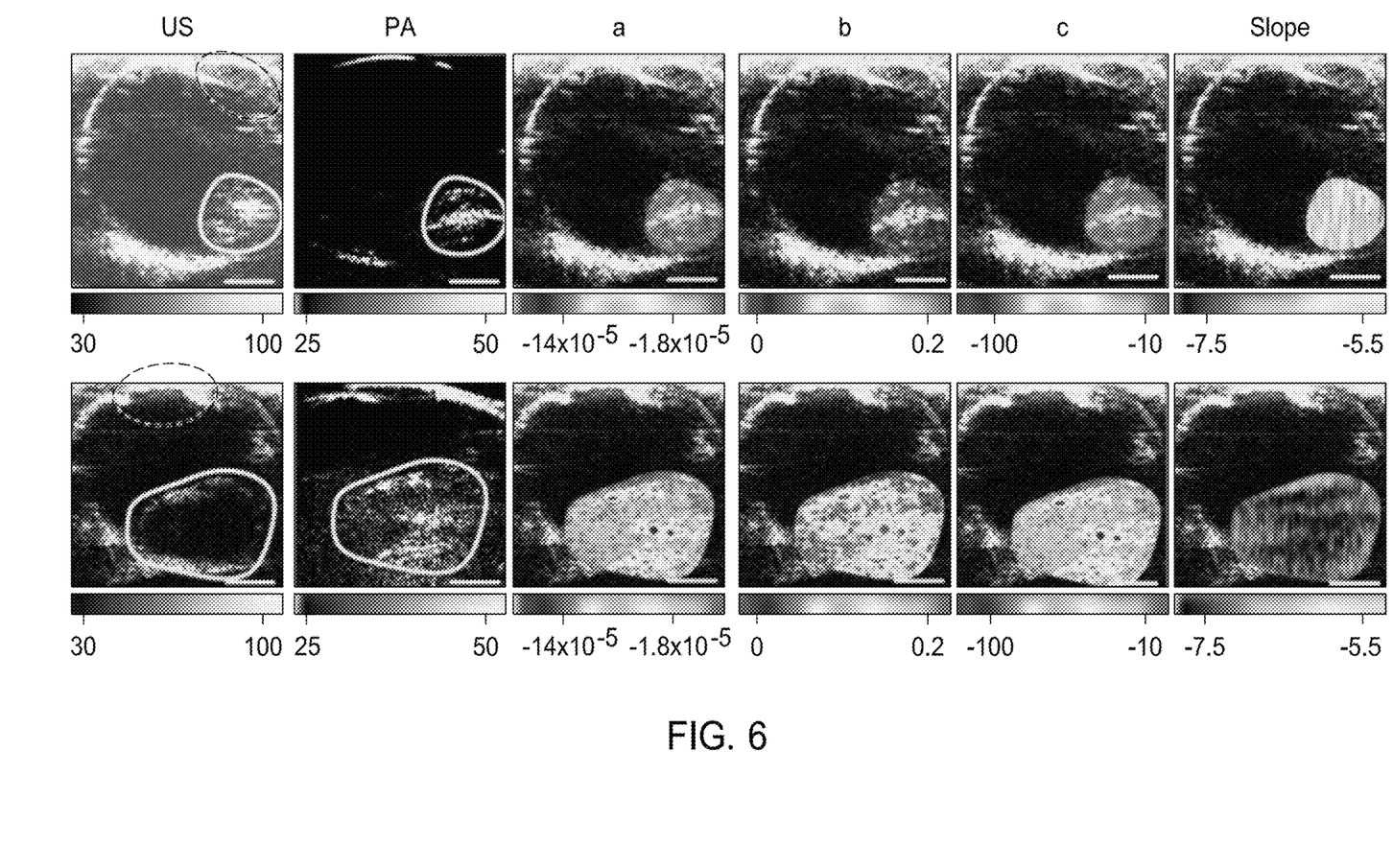
FIG. 6 illustrates representative US and PA images of ex vivo human ocular globes with retinoblastoma (top row) and choroidal melanoma (bottom row).

FIG. 6 illustrates the representative US and PA images of ex vivo human ocular globes with retinoblastoma (top row) and choroidal melanoma (bottom row). The dashed contours mark the iris areas with lenses. The solid contours mark the tumors. The pixel-wise optical spectral parameters (a, b, c and slope) will be explained in detail herein and PASA slopes within the tumor regions were calculated and coregistered to the US images. The units of the color axes for a, b, and c are arbitrary. The units of the color axis for slope is dB/MHz. Scale bar: 1 cm.

Quantifying the Optical Spectral Features

Figure 7A:
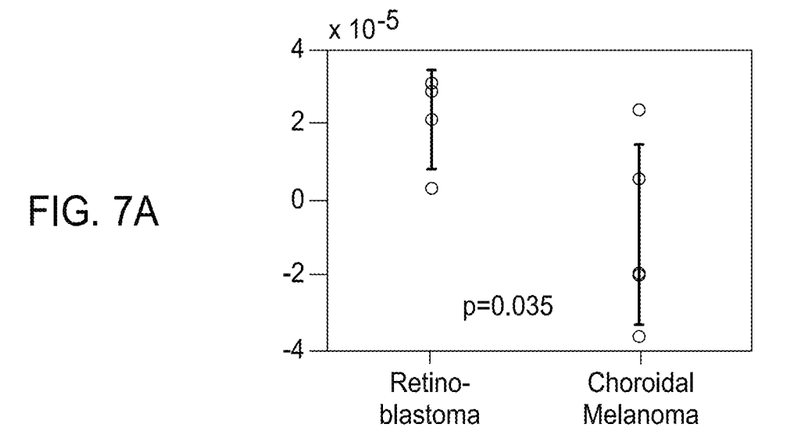
FIG. 7 illustrate statistical study of the quantitative features, i.e. a, b, and c of Equation 1, of the total optical absorption spectra.
Figure 7B:
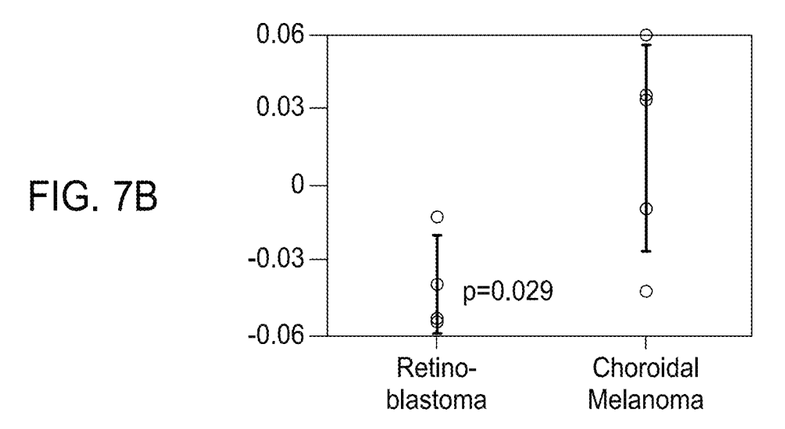
Figure 7C:
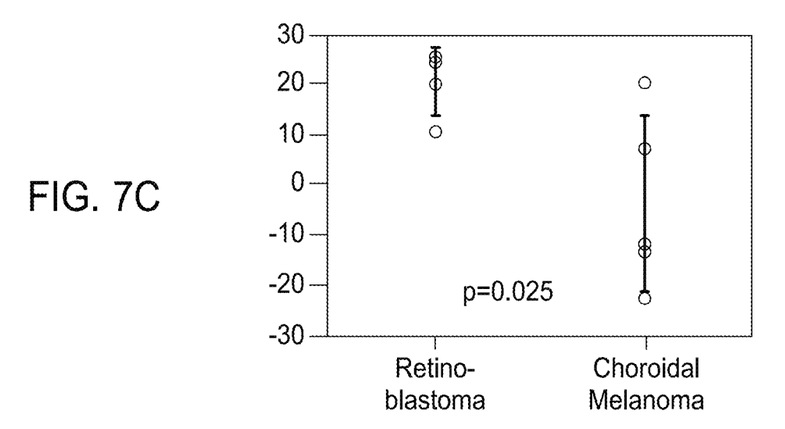

The optical absorption spectra of the intraocular tumors were quantified by fitting to a second order polynomial model:

$$S(w) = aw^2 + bw + c \quad (1)$$

Where S is the spectral magnitude; w is the wavelengths; a, b and c are the parameters defining the model. A single set of optical spectral parameters (a, b and c) were derived from each tumor, the statistics of which are shown in FIG. 7. The quantitative optical spectral parameters in Eq. (1) were also solved pixel-wise within the tumor regions to explicitly show the difference between retinoblastoma and choroidal melanoma. The power spectra calculated in each of the sliding window locations in the previous sections were revisited. By combining the signal power spectra at the same sliding window locations along the A-lines in the PA images at all wavelengths, pixel-wise PCSs were formed. The PCS of each sliding window location was quantified by Eq. (1). The pixel-wise optical spectral parameters in columns 3 to 5 in FIG. 6 were formed. Both the statistics in FIG. 7 and the color pixels in FIG. 6 show that the retinoblastoma has overall higher a and c values, as well as lower b values compared to those derived from the choroidal melanoma. Statistically significant differences were observed, supporting the potential of PAI in differentiating the two types of intraocular tumors.

Quantification of Ultrasonic Frequency Features in the PCSs

Figure 8A:
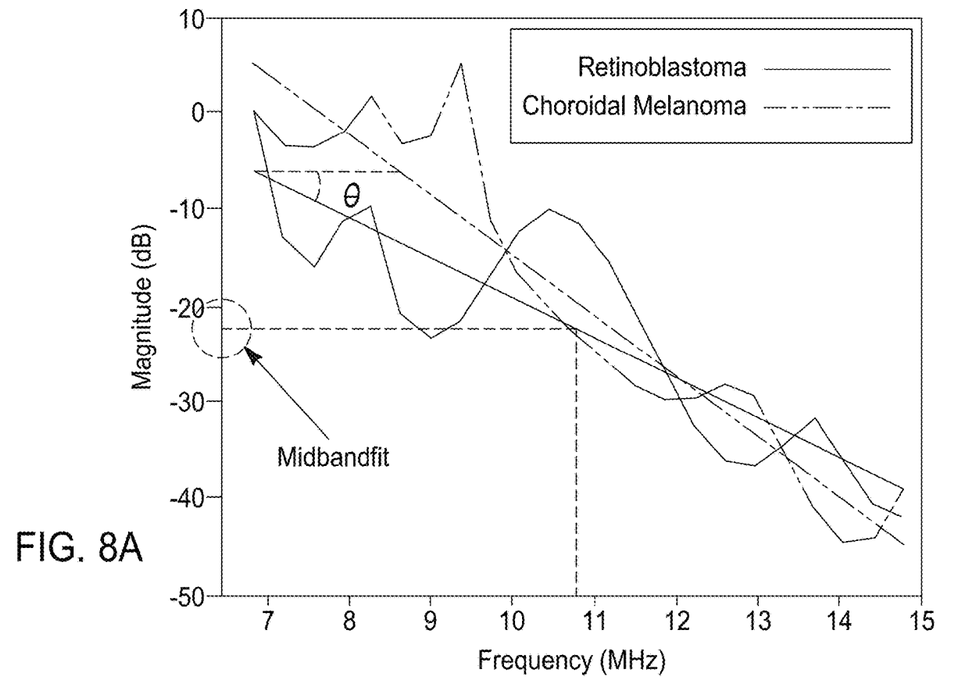
FIG. 8A is a PASA of a human intraocular tumors, with representative averaged PA signal spectra at 720 nm derived from the tumor samples. The solid lines are the linear fit to the signal power spectra within the probe frequency bandwidth (7-15 MHz). The PASA slope is tan(δ).
Figure 8B:
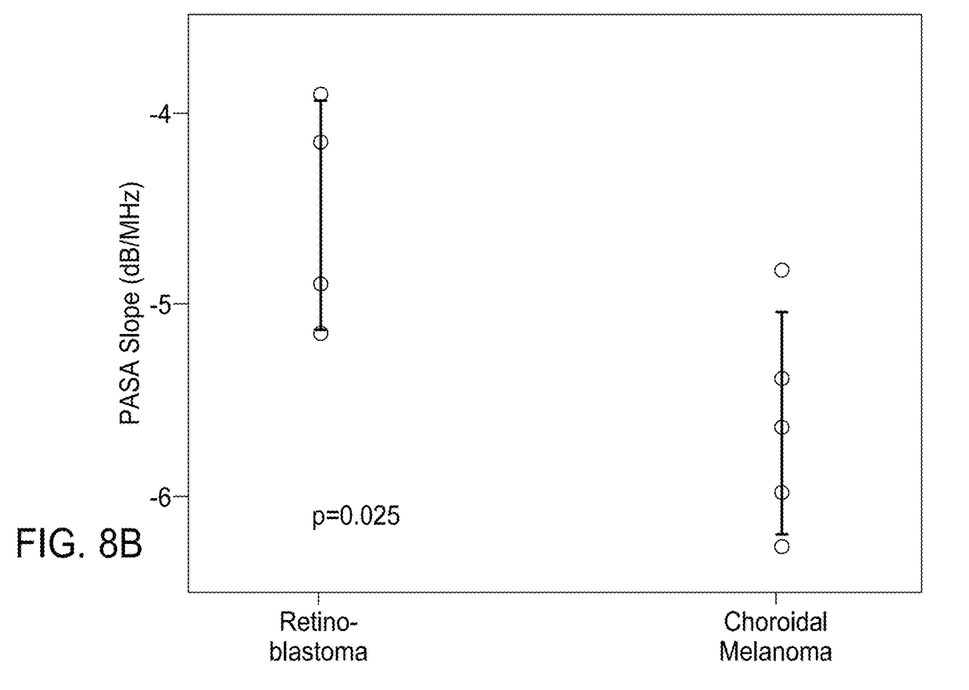
FIG. 8B is a graph illustrating statistics of the PASA slopes of retinoblastomas and choroidal melanomas. The slopes derived from choroidal melanomas have an average of −4.5 and standard deviation of 0.56. The slopes derived from retinoblastomas have an average of −5.6 and standard deviation of 0.60. Two-tailed t-test between the two groups has shown a p-value of 0.025.

PA spectral analysis (PASA), illustrated in FIG. 8A, was used in quantifying the descending trend of the pixel intensities along the y-axis in PCSs. Since both calcification (rich in retinoblastoma) and melanin (rich in choroidal melanoma) have strong optical absorption at 720 nm, PASA was implemented to the PCS vertical lines at this wavelength. In PASA, the power spectra were first fit to linear models. The slopes and the midband-fits of the linear models were quantified. The slope value is a measure of the ratio between high and low-frequency components in the PA signals. Larger slopes indicate more high-frequency components in the PA signals and thereby more heterogeneous tissue architecture in the samples. Midband-fit represents the overall magnitude of the PA power spectrum. Since the transducer array was only calibrated in 7-15 MHz, we focused on PASA slopes as a representation of the tissue heterogeneity. The summations of the pixels in PCS, instead of the midband-fits were used to quantify the total signal magnitude in the previous sections. Similar to the previous section, pixel-wise slopes were also calculated using the signal power spectra derived at each sliding window location and coregistered on top of the US images, as shown in FIG. 6 last column.

Discussion

Although the US and PA images shows similar structures, the contrast mechanism in the two imaging modalities are distinctive. The contrast of US is based on backscattered US waves. The bright eye globe contour is due to the reflected US waves. The retinoblastoma appear brighter than the uveal melanoma as a result of the heterogeneous tissue architecture in retinoblastoma. In the PA images, the bright eye globe contour is due to the dark color of the inner surface of the eye globe. The retinoblastoma and uveal melanoma are both bright as both the dominant chemical components in the tumors, the calcium and melanin, have strong optical absorption within the wavelength range used in this study.

The optical absorption spectrum of the retinoblastoma in mice was acquired in vivo and that of the retinoblastoma in human were acquired ex vivo. Optical absorption spectra of retinoblastoma in mice and human are comparable, indicating that the hemoglobin oxygenation level is not a significant factor to the optical absorption of retinoblastoma.

As discussed herein, intraocular tumors are life-threatening conditions. Long-term mortality from uveal melanoma, which accounts for 80% of primary intraocular tumors, could be as high as 25% depending on the size, histopathological and molecular biological features, ciliary body involvement and extraocular extension. The treatments of intraocular tumors include eye-sparing approaches such as radiotherapy and thermotherapy, and the more aggressive enucleation. The accurate diagnosis of intraocular tumors is thereby critical in the management and follow-up of the patients.

The diagnosis of intraocular tumors is usually based on clinical examination and imaging techniques such as ultrasonography which uses acoustic backscattering. By analyzing the high frequency fluctuations within the ultrasound (US) signals, microarchitecture information inside the tumor can be characterized. However, US cannot interrogate the histochemical components formulating the microarchitecture. One representative example is the inability of US imaging (and other contemporary imaging modalities as well) in differentiating nevoid and melanoma cells as the two types of cells possess similar acoustic backscattering properties. Combining optical and US imaging, photoacoustic (PA) measurements encode both the microarchitecture and histochemical component information in biological tissue.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically illustrated or described. The same may also be varied in many ways. Such variations are not to be regarded as a departure from the disclosure, and all such modifications are intended to be included within the scope of the disclosure.

What is claimed is:

1. A method of photoacoustic imaging of intraocular tumors, intraocular tumors being abnormal benign or malignant growth of tissue that possesses no physiological function and arises from uncontrolled cellular proliferation resulting in a lesion, the method comprising:

illuminating a lesion using a pulsed, wavelengths-tunable light source resulting in output of heat and thermoelastic expansion of components of the lesion, the thermoelastic expansion of the lesion producing propagating waves in ultrasonic frequencies;

acquiring the propagating waves using an ultrasound system and an array having a plurality of transducers and performing back-projection reconstruction thereby mapping the lesion components with optical contrast at ultrasonic resolution to image intraocular tumors of the lesion to produce an intraocular tumor image; and     analyzing the intraocular tumor image in frequency domain to output frequency domain power spectrum and fitting the frequency domain power spectrum to a linear model and quantifying a resultant slope to measure the heterogeneity of each of the lesion components and output microscopic architecture and histochemical component information of the intraocular tumors.

2. The method according to claim 1 wherein illuminating the lesion comprises illuminating the lesion with photoacoustic and ultrasound signals.

3. The method according to claim 1 wherein acquiring the propagating waves comprises employing a probe having a transducer array acquiring the propagating waves.

4. The method according to claim 3 wherein employing the probe comprises employing a probe having a convex ultrasound transducer array.

* * * * *